(12) United States Patent
Nishigaki

(10) Patent No.: US 9,307,954 B2
(45) Date of Patent: Apr. 12, 2016

(54) ULTRASOUND PROBE

(71) Applicant: Panasonic Corporation, Osaka (JP)

(72) Inventor: Morio Nishigaki, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 116 days.

(21) Appl. No.: 14/006,539

(22) PCT Filed: Nov. 1, 2012

(86) PCT No.: PCT/JP2012/007017
§ 371 (c)(1),
(2) Date: Sep. 20, 2013

(87) PCT Pub. No.: WO2013/065310
PCT Pub. Date: May 10, 2013

(65) Prior Publication Data
US 2014/0005552 A1 Jan. 2, 2014

(30) Foreign Application Priority Data

Nov. 2, 2011 (JP) .................................. 2011-240940

(51) Int. Cl.
*A61B 8/00* (2006.01)
*G10K 11/02* (2006.01)
*G10K 11/30* (2006.01)

(52) U.S. Cl.
CPC ............. *A61B 8/4477* (2013.01); *A61B 8/4444* (2013.01); *G10K 11/02* (2013.01); *G10K 11/30* (2013.01)

(58) Field of Classification Search
CPC .... A61B 8/4444; A61B 8/4477; G10K 11/02; G10K 11/30
See application file for complete search history.

(56) References Cited

U.S. PATENT DOCUMENTS

| 5,083,568 A | 1/1992 | Shimazaki et al. |
| 8,323,201 B2 * | 12/2012 | Towfiq et al. ................. 600/459 |
| 2004/0012307 A1 | 1/2004 | Fukuda et al. |

FOREIGN PATENT DOCUMENTS

| JP | 62-117539 A | 5/1987 |
| JP | 10-014916 A | 1/1998 |
| JP | 2003-175036 A | 6/2003 |
| JP | 2003-333693 A | 11/2003 |

OTHER PUBLICATIONS

International Search Report for corresponding International Application No. PCT/JP2012/007017 mailed Jan. 22, 2013.
(Continued)

*Primary Examiner* — Michael Rozanski
(74) *Attorney, Agent, or Firm* — Lucas & Mercanti, LLP

(57) ABSTRACT

An sound probe includes an array of transducer elements with a plurality of transducer elements arranged in a first direction and which makes an interconversion between an electric pulse and an ultrasonic wave; an acoustic lens with a convex surface in a transmission direction of the ultrasonic wave on a cross section that is parallel to the first direction and the transmission direction and which converges the ultrasonic waves transmitted from the plurality of transducer elements; and at least two acoustic adjustment layers made of a material that has a different sound velocity from the acoustic lens and arranged between at least two of the transducer elements. At least one of the material and a thickness of each of the at least two acoustic adjustment layers in the transmission direction are different from each other.

12 Claims, 10 Drawing Sheets

(56) References Cited

OTHER PUBLICATIONS

Form PCT/ISA/237 for corresponding International Application No. PCT/JP2012/007017 dated Jan. 22, 2013 and partial English translation.

Japanese Office Action; Application No. 2013-519905; Drafting Date: Jan. 15, 2015; Dispatch Date: Jan. 19, 2016; Representative: Kimihito Washida, et al; Applied Section(s); Section 29(2): total of 2 pages.

English translation of Japanese Patent Application; total of 4 pages.

* cited by examiner (a)

(b)

ULTRASONIC BEAM TRANSMISSION DIRECTION

ULTRASOUND PROBE

TECHNICAL FIELD

The present application relates to an sound probe for use in medical ultrasonic diagnostic apparatuses.

BACKGROUND ART

An ultrasonic diagnostic apparatus 100 includes an sound probe 101, a cable 102 and the apparatus body 103 as shown in FIG. 11. The sound probe 101 is connected to an electric circuit in the apparatus body 103 through the cable 102 and makes an interconversion on an ultrasonic wave and an electrical signal. The apparatus body 103 performs various kinds of signal processing including transmission processing in which a high-voltage transmission pulse to drive the sound probe 101 is output through the cable 102, reception processing in which a received signal, generated by the sound probe 101 on receiving an ultrasonic wave, is amplified to produce a received beam, brightness modulation of the received signal, and detecting blood flow information from the received signal, and generates an image signal based on the results of these kinds of signal processing.

FIG. 12 schematically illustrates the internal structure of the sound probe 101, which generally includes an array of transducer elements 104 where a plurality of transducer elements 105 are arranged in one direction. Signal lines are connected to the respective transducer elements 105 in the array of transducer elements 104 and bundled together to form the cable 102.

By getting the timings to apply the transmission pulses to those transducer elements 105 in the array of transducer elements 104 controlled by the apparatus body 103, an ultrasonic transmission beam to be emitted from this sound probe 101 can have any intended shape. On the other hand, by delaying the received signals obtained from these transducer elements 105 and then adding them together, an intended reception beam can be formed. As a result, a beam can be formed highly flexibly. For example, if the resolution in azimuth and direction (which will be sometimes referred to herein as "directivity") is sharpened by forming narrow transmission and reception beams, the image quality of the ultrasonic image can be improved.

In general, a transmission beam is formed in the direction in which the transducer elements 105 are arranged (which will be referred to herein as a "azimuth direction") by the technique described above. On the other hand, a transmission beam is shaped by an acoustic lens in the direction that intersects at right angles with the direction in which the transducer elements 105 are arranged and the depth direction in which ultrasonic waves are transmitted and received. The former direction will be referred to herein as a "elevation direction".

Next, it will be described with reference to FIG. 13 how to form a beam in the elevation direction. FIG. 13 illustrates a cross section of the sound probe 101 in the elevation direction (which will be referred to herein as a "short-axis cross section"). The transducer element 105 is one of the transducer elements included in the array of transducer elements 104. As shown in FIG. 13, a backing member 106 which attenuates the vibration of the transducer element 105 is arranged on the lower surface of the transducer element 105. On the upper surface of the transducer element 105, on the other hand, arranged is an acoustic matching layer 107 to reduce the difference in impedance between the transducer element 105 and the subject (not shown). And on the upper surface of the acoustic matching layer 107, arranged is an acoustic lens 108.

For example, if an acoustic lens 108 which is made of a material having a low sound velocity with respect to an organism is used, then the acoustic lens 108 may have such a shape as having a convex surface in the ultrasonic wave transmitting direction. As a result, the size of the transmission beam as measured in the elevation direction can be reduced.

A transmission beam is ordinarily converged so as to be narrowed at a certain depth level. In that case, at a level which is either shallower or deeper than the level at which the beam converges, the beam blurs so much that the azimuth resolution deteriorates.

When a transmission beam is shaped in the azimuth direction, the depth level at which the transmission beam converges can be changed by controlling the timing to apply a transmission drive pulse to the array of transducer elements 104 as described above. As a result, in the azimuth direction, the level at which the transmission beam narrows can be set in a broad range in the depth direction.

In the elevation direction, on the other hand, the transmission beam is shaped by the acoustic lens 108. That is why the transmission beam can be converged at only a particular depth level to be determined by the shape of the acoustic lens 108, and it is difficult to converge the transmission beam at any other depth level.

Thus, to overcome this problem, someone proposed a two-dimensional array of transducer elements which can change the depth levels at which an ultrasonic wave converges in both the azimuth and elevation directions by arranging a plurality of transducer elements in the elevation direction, too, and by controlling the timings to apply the transmission drive pulses. However, an sound probe 101 with such a two-dimensional array of transducer elements should have a great many transducer elements 105. That is why so many signal lines should be connected to such a huge number of transducer elements 105 that the cable 102 becomes too thick to use in practice. In addition, since the transmission beam is shaped two-dimensionally, the size of the electronic circuit needs to be increased, too.

Patent Document No. 1 discloses an sound probe which can overcome these problems. As shown in FIG. 14, the sound probe disclosed in Patent Document No. 1 includes transducer elements 105a, 105b and 105c which are arranged in the elevation direction. In observing a deep region of the subject using this sound probe, an ultrasonic wave is transmitted at a large aperture by using all of these transducer elements 105a to 105c. On the other hand, in observing a shallow region of the subject, an ultrasonic wave is transmitted at a small aperture by using only the transducer element 105b.

According to Patent Document No. 1, by using only the transducer element 105b, the transmission beam can be narrower than the conventional one and the resolution of the resultant tomographic image can be increased.

CITATION LIST

Literature

Patent Document No. 1: Japanese Laid-Open Patent Publication No. 62-117539

SUMMARY OF INVENTION

Technical Problem

According to the conventional technology described above, however, there is still a demand for further narrowing the transmission beam and further improving the image quality of the image obtained.

A non-limiting exemplary embodiment of the present application provides an sound probe which can reduce the width of a transmission beam in the elevation direction, too.

Solution To Problem

An sound probe according to the present disclosure includes: an array of transducer elements in which a plurality of transducer elements are arranged in a first direction and which makes an interconversion between an electric pulse and an ultrasonic wave; an acoustic lens which has a convex surface in a transmission direction of the ultrasonic wave on a cross section that is parallel to the first direction and the transmission direction and which converges the ultrasonic waves transmitted from the plurality of transducer elements; and at least two acoustic adjustment layers which are made of a material that has a different sound velocity from the acoustic lens, which are arranged between at least two of the transducer elements that are arranged in the first direction and the acoustic lens, and of which at least one of the material and a thickness of each of the at least two acoustic adjustment layers in the transmission direction are different from each other.

Another sound probe according to the present disclosure includes: an array of transducer elements in which a plurality of transducer elements are arranged in a first direction and which makes an interconversion between an electric pulse and an ultrasonic wave; an acoustic lens which has a convex surface in a direction in which the ultrasonic wave is transmitted on a cross section that is parallel to the first direction and the ultrasonic wave transmission direction and which converges the ultrasonic waves transmitted from the plurality of transducer elements; and an acoustic adjustment layer which is made of a material that has a different sound velocity from the acoustic lens and which is arranged between only some of the transducer elements that are arranged in the first direction and the acoustic lens.

In the array of transducer elements, the plurality of transducer elements may be arranged two-dimensionally in the first direction and in a second direction which is different from the first direction.

The acoustic adjustment layers may be made of a material which has a higher sound velocity than the acoustic lens. The closer to the center of the array of transducer elements in the first direction the transducer element associated with an acoustic adjustment layer is, the greater the thickness may be.

The at least two acoustic adjustment layers may include: a first acoustic adjustment layer which is associated with the transducer element that is located at the center of the array of transducer elements in the first direction; and a second acoustic adjustment layer which is adjacent to the first acoustic adjustment layer in the first direction. The first acoustic adjustment layer may be thicker than the second acoustic adjustment layer.

The acoustic adjustment layers may be made of a material which has a lower sound velocity than the acoustic lens. The closer to the center of the array of transducer elements in the first direction the transducer element associated with an acoustic adjustment layer is, the smaller the thickness may be.

The at least two acoustic adjustment layers may include: a first acoustic adjustment layer which is associated with the transducer element that is located at the center of the array of transducer elements in the first direction; and a second acoustic adjustment layer which is adjacent to the first acoustic adjustment layer in the first direction. The first acoustic adjustment layer may be less thick than the second acoustic adjustment layer.

The acoustic adjustment layers may be made of a material which has a higher sound velocity than the acoustic lens. The closer to the center of the array of transducer elements in the first direction the transducer element associated with an acoustic adjustment layer is, the higher the sound velocity of the material of that acoustic adjustment layer may be.

The acoustic adjustment layers may be made of a material which has a lower sound velocity than the acoustic lens. The farther away from the center of the array of transducer elements in the first direction the transducer element associated with an acoustic adjustment layer is, the lower the sound velocity of the material of that acoustic adjustment layer may be.

The acoustic adjustment layers may be made of a material having an acoustic impedance which is either the same as, or close to, the acoustic impedance value of the acoustic lens.

The acoustic lens may include: a first acoustic lens portion, of which the surface shape has a first curvature on a cross section which is parallel to the first direction and the transmission direction; and a second acoustic lens portion which is arranged on the first acoustic lens in the transmission direction and of which the surface shape has a second curvature.

The second curvature may be larger than the first curvature.

The first and second acoustic lens portions may be made of the same material.

Advantageous Effects Of Invention

The sound probe according to the present disclosure can make the transmission beam sufficiently narrow even at a deep level inside the subject, and therefore, can obtain an ultrasonic image of good image quality.

DESCRIPTION OF EMBODIMENTS

The present inventors checked out minutely the characteristic of the conventional sound probe disclosed in Patent Document No. 1, for example. As a result, the present inventors discovered that when an ultrasonic wave was transmitted at an increased aperture using the sound probe of Patent Document No. 1, the transmission beam could not be narrow enough in the elevation direction at some deep level in the transmission direction.

Figure 14:
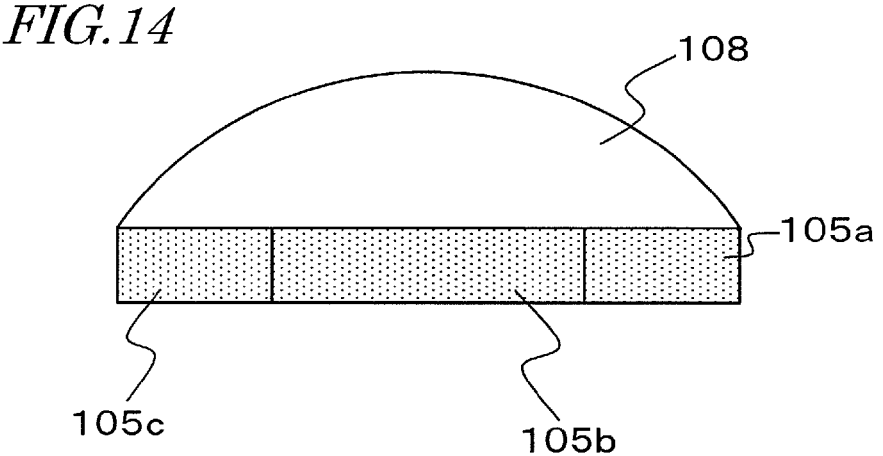
FIG. 14 is a cross-sectional view illustrating still another conventional sound probe.

The present inventors discovered and confirmed via experiments that if the acoustic lens 108 had a convex surface, the propagation distance of the ultrasonic wave transmitted from the transducer element 105b through the acoustic lens 108 became longer than that of the ultrasonic wave transmitted from the transducer element 105a or 105c through the acoustic lens 108 as shown in FIG. 14. Thus, we discovered that (if the acoustic lens 108 had a lower ultrasonic wave propagation velocity (i.e., a lower sound velocity) than the subject), the ultrasonic wave transmitted from the transducer element 105a or 105c reached the subject earlier than the ultrasonic wave transmitted from the transducer element 105b, thus disturbing the convergence of the coverging transmission beam and splitting the transmission beam into two and expanding them particularly in the elevation direction at a deep level in the transmission direction.

Thus, to overcome these problems, the present inventors invented an sound probe with a novel structure which can narrow the transmission beam sufficiently even at a relatively deep level, in particular, and which can obtain an ultrasonic image of good image quality as a result. Hereinafter, embodiments of an sound probe according to the present invention will be described with reference to the accompanying drawings.

Embodiment 1

Figure 1A:
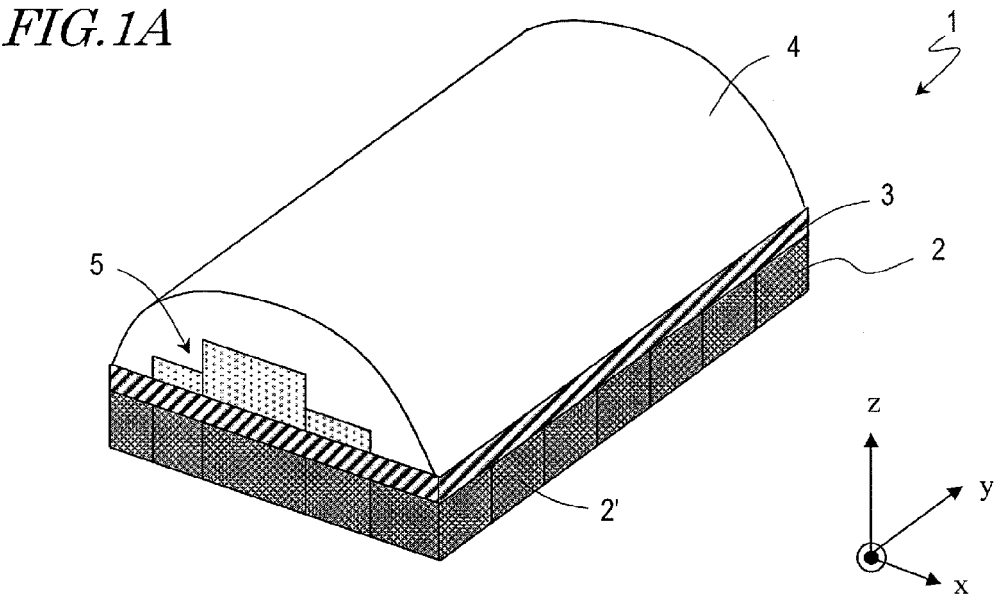
FIG. 1A is a perspective view illustrating a portion of an sound probe as a first embodiment of the present invention.

FIG. 1A is a perspective view illustrating a first embodiment of an sound probe according to the present invention. This sound probe 1 includes an array of transducer elements 2, an acoustic matching layer 3, an acoustic lens 4 and an acoustic adjustment layer 5. As shown in FIG. 1A, the array of transducer elements 2 includes a plurality of transducer elements 2' which are arranged two-dimensionally in the x direction (first direction) and y direction (second direction). These x- and y-axis directions correspond to the elevation and azimuth directions, respectively. Although not shown in FIG. 1A, each of these transducer elements 2' is connected to a signal line as in the conventional sound probe. Those signal lines are bundled together into a cable and electrically connected to the body of the ultrasonic diagnostic apparatus (not shown). Each of these transducer elements 2' is a transducer which makes an interconversion between an electric pulse and an ultrasonic wave and may be implemented as a piezoelectric element.

In response to an electric pulse applied to the array of transducer elements 2 through the cable, each of the transducer elements 2' in the array of transducer elements 2 vibrates and an ultrasonic wave is transmitted from the transducer element 2'. The ultrasonic wave passes through the acoustic matching layer 3, gets converged by the acoustic lens and then is transmitted in the z-axis direction (the ultrasonic wave transmission direction).

Figure 1B:
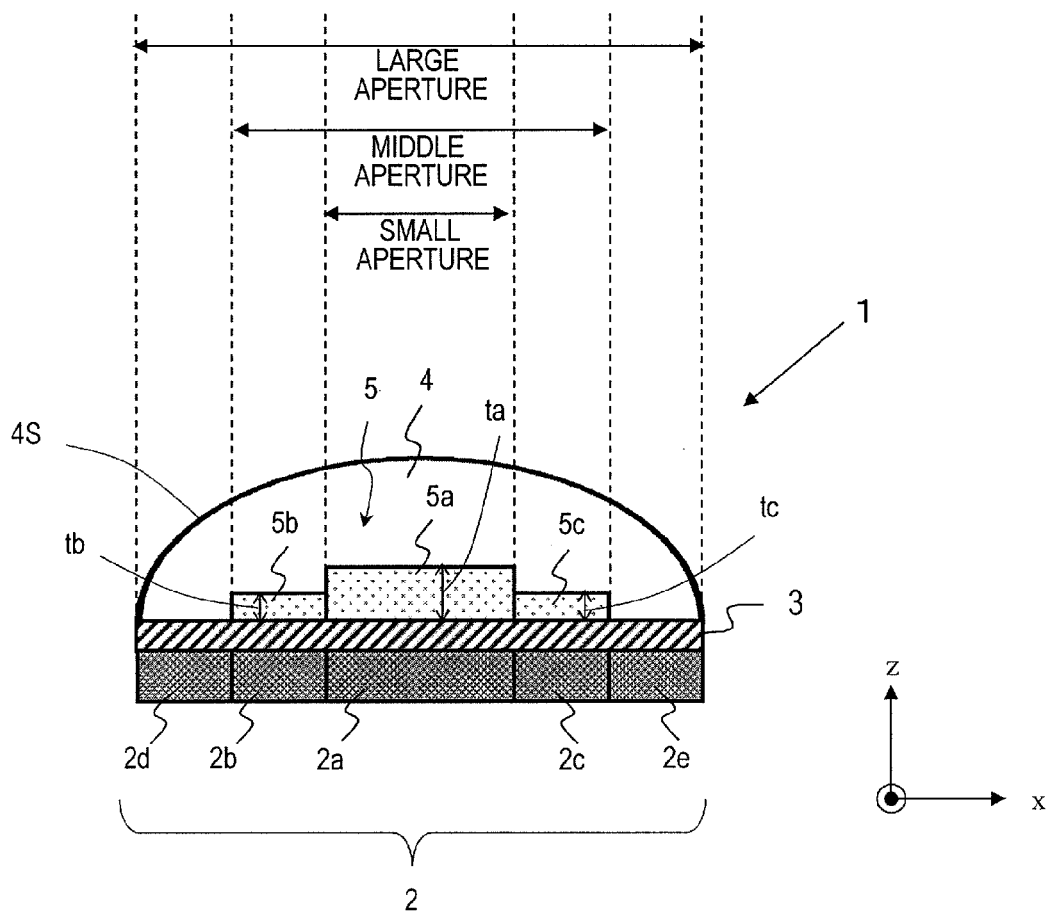
FIG. 1B is a cross-sectional view illustrating the portion of the sound probe according to the first embodiment of the present invention.

FIG. 1B illustrates a cross section of the sound probe 1 which is parallel to the x- and z-axis directions.

The array of transducer elements 2 includes transducer elements 2a, 2b, 2c, 2d and 2e, which are a plurality of transducer elements 2' arranged in the x-axis direction. Optionally, a backing member (not shown) which attenuates the vibration of these transducer elements 2a through 2e may be provided on the lower surface of the transducer elements 2a to 2e. On the other hand, on the upper surface of the transducer elements 2a to 2e, an acoustic matching layer 3 which reduces the difference in acoustic impedance between the transducer elements 2a to 2e and the subject may be provided. On the upper surface of the acoustic matching layer 3, arranged is the acoustic lens 4. As shown in FIG. 1B, the acoustic lens 4 is convex in the z-axis direction of the ultrasonic wave and toward the outside of this sound probe 1. That is to say, the surface 4s is convex in the z-axis direction.

In addition, an acoustic control structure 5 is arranged between the transducer elements 2a to 2e and the acoustic lens 4. The acoustic control structure 5 is located between at least two transducer elements and the acoustic lens 4. In this embodiment, the acoustic control structure 5 includes acoustic adjustment layers 5a, 5b and 5c which are respectively arranged between the transducer elements 2a, 2b and 2c and the acoustic lens 4. The acoustic adjustment layers 5a, 5b and 5c are made of a material with a higher sound velocity than the material of the acoustic lens 4. Also, in this embodiment, these acoustic adjustment layers 5a, 5b and 5c are made of the same material.

In order to make the ultrasonic waves propagate smoothly, the material of the acoustic adjustment layers 5a, 5b and 5c and the material of the acoustic lens 4 suitably have the same or close acoustic impedance values. In this description, if two acoustic impedance values are close to each other, then it means herein that the ratio of the acoustic impedance of the material of the acoustic adjustment layers 5a, 5b and 5c to the acoustic impedance of the material of the acoustic lens 4 falls within the range of approximately 0.5 to 1.5. In general, silicone rubber with an acoustic impedance of about 1.5 with respect to the acoustic impedance of the subject is often used as the material of the acoustic lens 4. That is why by using a material of which the acoustic impedance ratio falls within this range, ultrasonic waves can propagate efficiently with reflection of the ultrasonic waves from the interface between the two materials minimized.

Furthermore, in this embodiment, the material of the acoustic adjustment layers 5a, 5b and 5c has a higher sound velocity than the material of the acoustic lens 4. If silicone rubber is used as the material of the acoustic lens 4, silicon rubber to which a filler such as zinc oxide or titanium oxide has been added may be used as the material of the acoustic adjustment layers 5a, 5b and 5c. Alternatively, an epoxy resin, of which the acoustic impedance is close to that of silicone rubber, may also be selected. However, these materials are only examples and the acoustic lens 4 and the acoustic adjustment layers 5a, 5b and 5c may also be made of any other material.

As shown in FIG. 1B, the length (or width) of the acoustic adjustment layer 5a as measured in the x-axis direction is substantially as large as the length of the transducer element 2a as measured in the x-axis direction. Also, the acoustic adjustment layer 5a is arranged so that both end faces of the acoustic adjustment layer 5a are substantially aligned with the boundary between the transducer elements 2a and 2b and the boundary between the transducer elements 2a and 2c as indicated by the dotted lines in FIG. 1B.

Likewise, the lengths of the acoustic adjustment layers 5b, 5c as measured in the x-axis direction are substantially as large as the lengths of the transducer elements 2b, 2c, respectively. Also, the acoustic adjustment layer 5b is arranged so that both end faces of the acoustic adjustment layer 5b are substantially aligned with the boundary between the transducer elements 2a and 2b and the boundary between the transducer elements 2b and 2d. The acoustic adjustment layer 5c is arranged so that both end faces of the acoustic adjustment layer 5c are substantially aligned with the boundary between the transducer elements 2a and 2c and the boundary between the transducer elements 2c and 2e. That is to say, these acoustic adjustment layers 5a, 5b and 5c are arranged so as to process the ultrasonic waves that have been transmitted from the transducer elements 2a, 2b and 2c, respectively.

In this embodiment, the closer to the center of the array of transducer elements 2 in the x-axis direction the transducer element associated with an acoustic adjustment layer is, the greater the thickness of that acoustic adjustment layer as measured in the z-axis direction is. More specifically, the acoustic adjustment layer 5a associated with the transducer element 2a that is located at the center of the array of transducer elements 2 in the x-axis direction has a greater thickness as measured in the z-axis direction than any of the other acoustic adjustment layers 5b and 5c associated with the transducer elements 2b and 2c that are located farther away from the center of the array of transducer elements 2. That is to say, if the thicknesses of the acoustic adjustment layers 5a, 5b and 5c are identified by ta, tb and tc, respectively, ta>tb and ta>tc are satisfied. In this embodiment, tb and tc are substantially equal to each other.

In transmitting an ultrasonic wave to a relatively shallow level in the subject to capture an image of that shallow level, the sound probe 1 drives only the transducer element 2a. On the other hand, in transmitting an ultrasonic wave to a relatively deep level in the subject to capture an image of that deep level, the sound probe 1 drives all of these transducer elements 2a to 2e. Furthermore, in transmitting an ultrasonic wave to an intermediate level between them to capture an image of that intermediate level, the sound probe 1 drives the transducer elements 2a to 2c.

The acoustic lens 4 has a convex surface 4s in the transmission direction on a cross section which intersects with the x- and z-axis directions at right angles. That is why the distance as measured in the z-axis direction from the upper surface of the transducer element 2a to 2e to the surface 4s of the acoustic lens 4 becomes longer in the center portion in the x-axis direction than in the end portions. However, the acoustic adjustment layers 5a, 5b and 5c which are made of a material with a higher sound velocity than the acoustic lens 4 are arranged between the transducer elements 2a to 2e and the acoustic lens 4.

When measured in the z-axis direction, the thickness of the acoustic adjustment layer 5a located at the center in the x-axis direction is greater than those of the acoustic adjustment layers 5b and 5c located closer to the end portions than the acoustic adjustment layer 5a is. That is why these acoustic adjustment layers 5a, 5b and 5c function so as to reduce the difference in arrival time, or in phase, between the ultrasonic waves due to the difference between the respective transducer elements 2a to 2e in the distance from their upper surface to the surface 4s of the acoustic lens 4 according to their locations in the x-axis direction. Thus, the ultrasonic waves that have come from the transducer elements 2a to 2e to be emitted through the surface 4s of the acoustic lens 4 come to have a reduced phase difference and will arrive at the subject at less different times. As a result, if ultrasonic waves have been transmitted from all of these transducer elements 2a through 2e, the phase difference between the transmitted beams to converge can be reduced and it is possible to prevent any transmitted beam from being split into two and expanding at a deep level in the transmission direction. Consequently, an ultrasonic beam which is sufficiently narrow even at a deep level can be transmitted to the subject, and an ultrasonic image can be obtained at a high resolution.

The present inventors carried out simulations to confirm the effects achieved by the sound probe 1 of this embodiment. The results are as follows.

FIGS. 2(a) and 2(b) show the results of the simulations on the beam shape in the x-axis direction of the sound probe of this embodiment and a conventional sound probe. The center frequency of transmission is approximately 9 MHz.

The material of the acoustic lens 4 of the sound probe 1 that was used in the simulations of FIG. 2(a) has a sound velocity of 1000 m/s. The surface shape of the acoustic lens 4 has a radius of curvature of 10 mm. Also, as measured in the x-axis direction, the transducer element 2a has a length of 2.8 mm, the transducer elements 2b and 2c have a length of 0.6 mm, and the transducer elements 2d and 2e have a length of 1.1 mm. If an ultrasonic wave is transmitted using only the transducer element 2a, the aperture width becomes 2.8 mm (which will be referred to herein as a "small aperture"). If an ultrasonic wave is transmitted using the transducer elements 2a to 2c, the aperture width becomes 4.0 mm (which will be referred to herein as a "middle aperture"). And if an ultrasonic wave is transmitted using the transducer elements 2a to 2e, the aperture width becomes 6.2 mm (which will be referred to herein as a "large aperture").

The acoustic adjustment layers 5a to 5c are made of a material with a sound velocity of 1500 m/s. When measured in the z-axis direction, the acoustic adjustment layer 5a has a thickness of 0.12 mm and the acoustic adjustment layers 5b and 5c each have a thickness of 0.06 mm. The simulations were carried out on the supposition that the acoustic adjustment layers 5a to 5c were made of a material with the same acoustic impedance as the acoustic lens 4.

The conventional sound probe used in the simulations of FIG. 2(b) has the same structure as the sound probe 1 used in the simulations of FIG. 2(a) except that the conventional sound probe has no acoustic adjustment layers.

Figure 2:
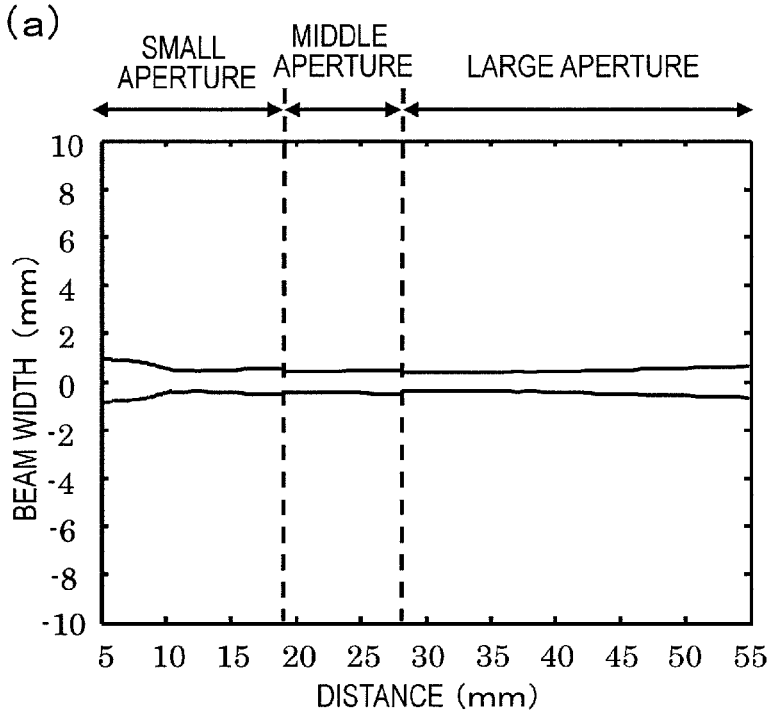
FIGS. 2(a) and 2(b) show the results of simulations on the beams transmitted by the sound probe of the first embodiment and a conventional sound probe.
Figure 2:
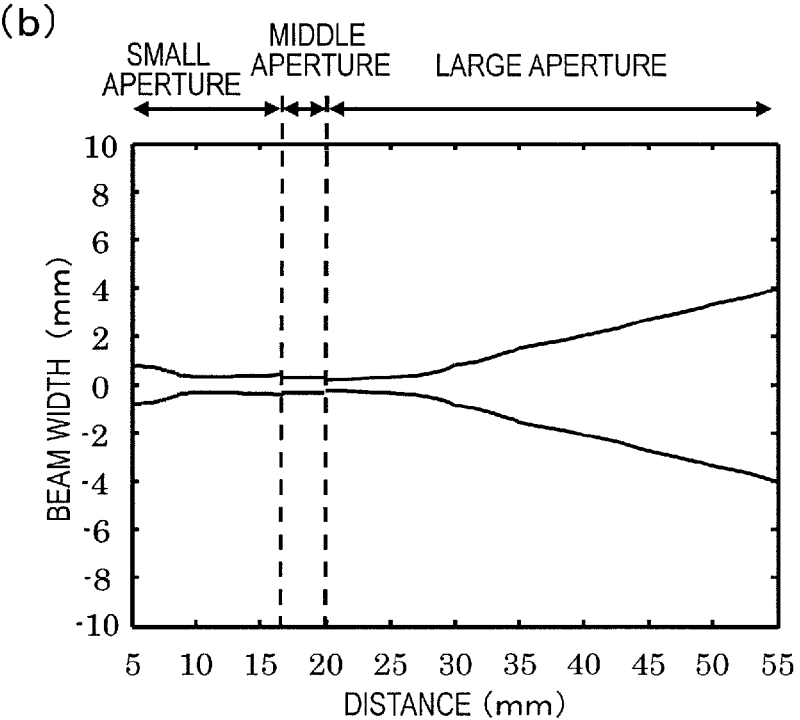

The results of the simulations shown in FIGS. 2(a) and 2(b) were obtained in the following manner. Specifically, a position with the highest ultrasonic wave intensity at a certain depth level (i.e., at a certain position in the Z-axis direction) was supposed to be the origin (0 dB) and a position (or distance (mm)) with an ultrasonic wave intensity corresponding to −3 dB with respect to the origin was plotted in the x-axis direction at that position in the Z-axis direction. By setting these positions at an arbitrary depth level, a beam profile in the depth direction was obtained. That is why in FIG. 2, the abscissa indicates the distance (mm) as measured from the sound probe 1 in the depth direction in which ultrasonic waves are transmitted and the ordinate indicates the width (mm) of a beam at which an intensity of −3 dB can be obtained with respect to the center of the beam.

Also, the results of the simulations shown in FIGS. 2(a) and 2(b) were obtained by getting data about depth levels of 5 to 55 mm in the respective cases of small, middle and large apertures, extracting data about ranges where the transmitted beams with the small, middle and large apertures were sufficiently converged, and synthesizing those data together.

As shown in FIG. 2(a), the sound probe 1 of this embodiment can converge the transmitted beam at almost every depth, no matter whether the beam has a small, middle or large aperture.

On the other hand, as shown in FIG. 2(b), in the conventional sound probe, at a depth of approximately 25 mm or more, the width of the ultrasonic beam transmitted through the large aperture expands steeply. Thus, it can be seen that in the case of the large aperture, the transmitted beam cannot be converged sufficiently particularly at a deep level.

Although not shown, if the radius of curvature of the acoustic lens is increased in the conventional sound probe, the beam shape at a deep level becomes a narrow one in the case of the large aperture. In that case, however, the beam shape at a shallow level becomes a wide one in the case of the small aperture. That is to say, it is difficult for the conventional sound probe to form a narrow transmitted beam at both of shallow and deep levels.

As can be seen from these results of simulations, the sound probe 1 of this embodiment can converge the transmitted beam sufficiently even at a relatively deep level, and therefore, can converge the transmitted beam in a broader range in the depth direction than the conventional sound probe. Consequently, an ultrasonic image of good image quality can be obtained in a broader range.

In this embodiment, no acoustic adjustment layers are provided for the transducer elements $2d$ and $2e$. However, as long as the condition that ultrasonic waves transmitted simultaneously from the transducer elements $2a$ to $2e$ arrive at a certain depth level at as close to the same time as possible is satisfied, acoustic adjustment layers may be provided for the transducer elements $2d$ and $2e$, too. In that case, when measured in the z-axis direction, the thickness of the acoustic adjustment layers provided for the transducer elements $2d$ and $2e$ is set to be smaller than the thicknesses tb, tc of the acoustic adjustment layers $5b$ and $5c$ associated with the transducer elements $2b$ and $2c$ which are adjacent to, and located closer to the center of the sound probe 1 than, the transducer elements $2d$ and $2e$ in the x-axis direction.

The sound probe 1 of this embodiment includes the acoustic adjustment layers $5a$ to $5c$, which are made of a material with a higher sound velocity than the acoustic lens 4, thus shortening the time it takes for ultrasonic waves transmitted from the transducer elements $2a$ to $2c$ of the sound probe 1 to reach an intended depth level via the acoustic lens 4 compared to a situation where no acoustic adjustment layers are provided. In addition, since the acoustic lens 4 has a convex surface in the ultrasonic wave transmission direction, the ultrasonic wave can reach the acoustic lens 4 in a shorter time by adjusting the thicknesses of the acoustic adjustment layers so that the closer to the center of the array of transducer elements the transducer element associated with an acoustic adjustment layer is, the greater the thickness of that acoustic adjustment layer is. Consequently, even if the ultrasonic waves transmitted simultaneously from the transducer elements $2a$ to $2e$ propagate through the acoustic lens 4 which has such a convex surface in the ultrasonic wave transmission direction, those ultrasonic waves can still reach a certain depth level in the subject at as close to the same time as possible.

Such an ultrasonic wave propagation time adjustment can also be made even by providing acoustic adjustment layers $5a$ to $5c$ which are made of a material with a lower sound velocity than the acoustic lens 4. Specifically, if the acoustic adjustment layers are made of a material with a higher sound velocity than the acoustic lens 4, then the thicknesses of the acoustic adjustment layers may be adjusted so that the closer to the center of the array of transducer elements in the x-axis direction the transducer element associated with an acoustic adjustment layer is, the smaller the thickness of that acoustic adjustment layer is (i.e., so that the farther away from the center of the array of transducer elements the transducer element associated with an acoustic adjustment layer is, the greater the thickness of that acoustic adjustment layer is).

Figure 3A:
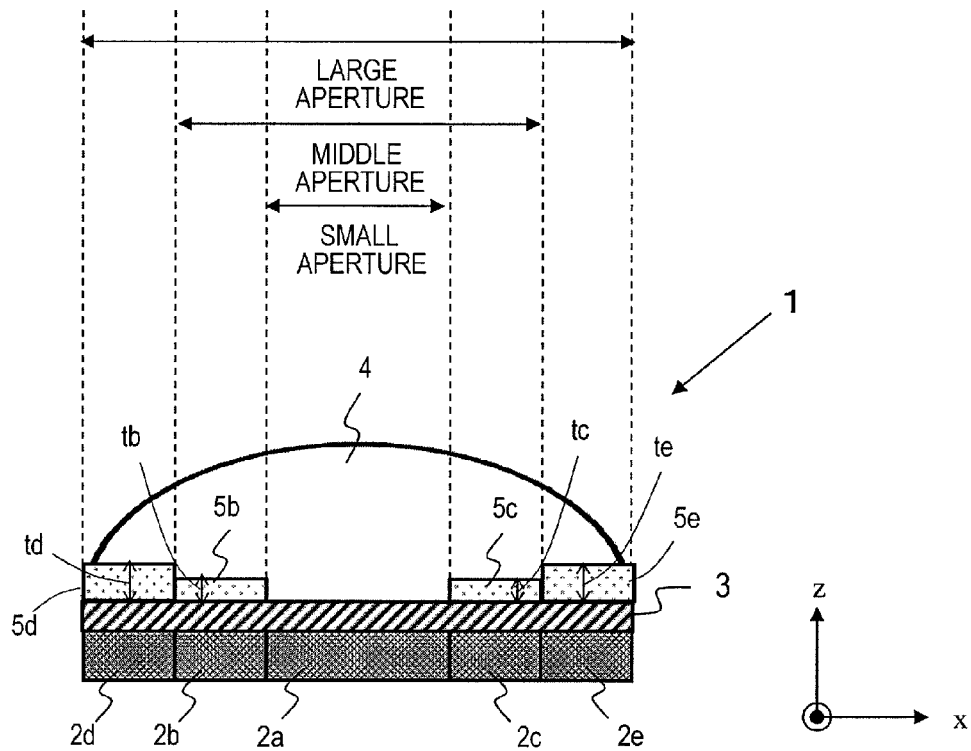
FIG. 3A is a cross-sectional view illustrating another example of the first embodiment.

More specifically, acoustic adjustment layers $5b$ to $5e$ which are made of a material with a lower sound velocity than the acoustic lens 4 are used as shown in FIG. 3A. The acoustic adjustment layers $5b$ to $5e$ are arranged on, and associated with, the transducer elements $2b$ to $2e$, respectively.

Since the sound velocity in the acoustic adjustment layers $5b$ to $5e$ is lower than the sound velocity in the acoustic lens 4, the ultrasonic waves being transmitted through these acoustic adjustment layers $5b$ to $5e$ propagate in a longer time. That is why by providing no associated acoustic adjustment layer for the transducer element 2 located at the center in the x-axis direction, the ultrasonic wave can reach the acoustic lens 4 in a relatively short propagation time. On top of that, if the thicknesses td and to of the acoustic adjustment layers $5d$ and $5e$ which are located farther away from the center than the acoustic adjustment layers $5b$ and $5c$ are set to be greater than the thicknesses tb and tc of the acoustic adjustment layers $5b$ and $5c$, the ultrasonic waves transmitted from the transducer elements $2b$ and $2c$ can reach earlier than the ultrasonic waves transmitted from the transducer elements $2d$ and $2e$. As a result, the closer to the center the transducer element that has transmitted the ultrasonic wave is, the shorter the propagation time it takes for the ultrasonic wave to reach the acoustic lens 4. Consequently, even if the ultrasonic waves transmitted simultaneously from the transducer elements $2a$ to $2e$ propagate through the acoustic lens 4 having such a convex surface in the ultrasonic wave transmission direction, those ultrasonic waves can still reach a certain depth level in the subject at as close to the same time as possible.

Figure 3B:
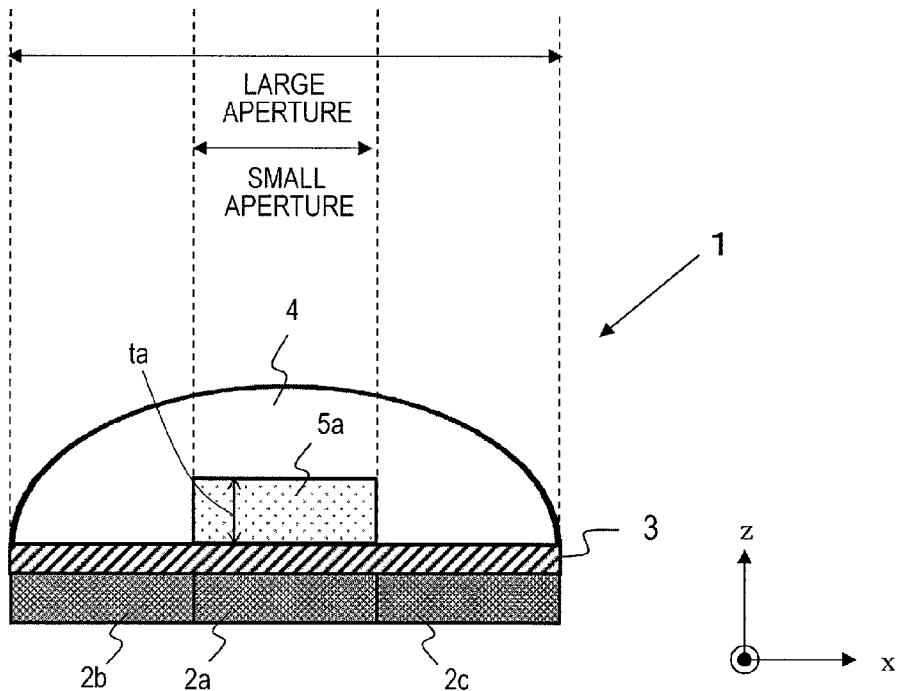
FIG. 3B is a cross-sectional view illustrating still another example of the first embodiment.

In the embodiment described above, the sound probe is supposed to be able to transmit ultrasonic waves with the sizes of the aperture changed between large, middle and small ones. However, an sound probe which transmits ultrasonic waves with the sizes of the aperture changed between large and small ones may also be implemented. In that case, if an acoustic adjustment layer $5a$ made of a material with a higher sound velocity than the acoustic lens 4 is arranged on the upper surface of the transducer element 2 as shown in FIG. 3B, the effects of the embodiment described above can also be achieved. Optionally, although not shown, acoustic adjustment layers $5b$ and $5c$ which are made of a material with a lower sound velocity than the acoustic lens 4 may be arranged on the upper surface of the transducer elements $2b$ and $2c$ as well. That is to say, acoustic adjustment layer(s) made of a material with a different sound velocity from the acoustic lens 4 may be arranged between only some of the transducer elements arranged in the x-axis direction and the acoustic lens 4.

Embodiment 2

The first embodiment described above is an sound probe which can narrow the beam width sufficiently even at a relatively deep level in the beam converging direction by using acoustic adjustment layers. A second embodiment to be described below is an sound probe which can further narrow the beam width in a broad range from a relatively shallow level to a relatively deep level.

Figure 4:
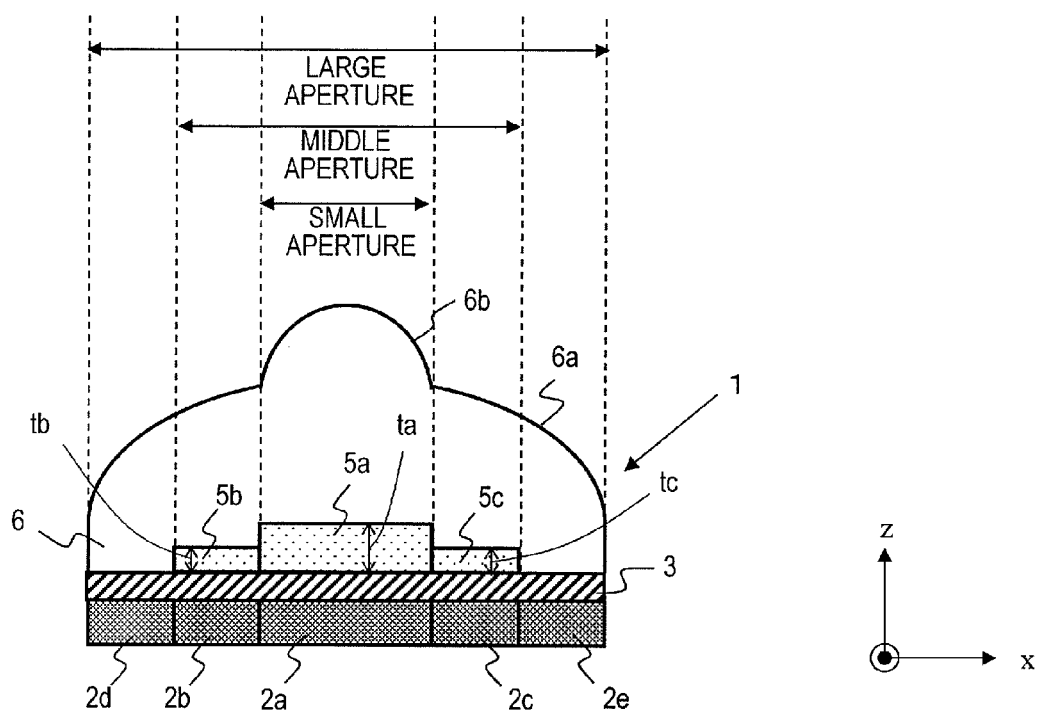
FIG. 4 is a cross-sectional view illustrating a portion of an sound probe as a second embodiment of the present invention.

FIG. 4 illustrates an x-axis cross section of an sound probe 1 according to this embodiment. This sound probe includes an array of transducer elements, including transducer elements 2a to 2e, an acoustic adjustment layer 5 and an acoustic lens 6. The array of transducer elements 2 and the acoustic adjustment layer 5 have the same structure and are made of the same material as the counterparts of the sound probe 1 of the first embodiment described above.

The sound probe 1 of the first embodiment described above includes an acoustic lens 4 which has a single curvature and which has a convex surface in the ultrasonic wave transmission direction. On the other hand, the acoustic lens 6 of the sound probe 1 of this embodiment has a convex surface shape with two different curvatures.

More specifically, the acoustic lens 6 includes a first acoustic lens portion 6a having a surface shape with a first curvature and a second acoustic lens portion 6b having a surface shape with a second curvature. The second curvature is larger than the first curvature and the first and second acoustic lens portions 6a and 6b are made of the same material. The first and second acoustic lens portions 6a and 6b may be formed separately and then bonded together or may be formed as an integral part.

As shown in FIG. 4, the first acoustic lens portion 6a is arranged to face the transducer elements 2a to 2e with the acoustic adjustment layers 5a to 5c interposed in the ultrasonic wave transmission direction. On the other hand, the second acoustic lens portion 6b faces the transducer element 2a and is arranged over the first acoustic lens portion 6a (i.e., closer to the subject or an external device in the z-axis direction) so that an ultrasonic wave transmitted from the transducer element 2a enters the second acoustic lens portion 6b. More specifically, the second acoustic lens portion 6b is arranged over the first acoustic lens portion 6a in the ultrasonic wave transmission direction so that the boundary between the first and second acoustic lens portions 6a and 6b is substantially aligned with the boundary between the transducer elements 5a and 5b and the boundary between the transducer elements 5a and 5c in the x-axis direction as indicated by the dotted lines in FIG. 4.

By using an acoustic lens 6 with such a structure, the beam width can be sufficiently narrow in a broad range from a relatively shallow level to a deep level even if the aperture size is decreased.

The present inventors carried out simulations to confirm the effects achieved by the sound probe 1 of this embodiment. The results will be described below. In the following description, the results of the simulations obtained for the sound probe 1 of the first embodiment will be referred to again in order to describe the difference between this and first embodiments easily understandably. The center frequency of ultrasonic waves to be transmitted from the sound probe is approximately 9 MHz.

FIGS. 5(a) and 5(b) show the results of the simulations on the beam shape in the x-axis direction of the sound probe of this embodiment and the sound probe of the first embodiment, respectively.

As in the first embodiment described above, the material of the acoustic lens 4, 6 of the sound probe 1 that was used in the simulations has a sound velocity of 1000 m/s. Also, as measured in the x-axis direction, the transducer element 2a has a length of 2.8 mm, the transducer elements 2b and 2c have a length of 0.6 mm, and the transducer elements 2d and 2e have a length of 1.1 mm.

Also, as in the first embodiment described above, the acoustic adjustment layers 5a to 5c are made of a material with a sound velocity of 1500 m/s. When measured in the z-axis direction, the acoustic adjustment layer 5a has a thickness of 0.12 mm and the acoustic adjustment layers 5b and 5c each have a thickness of 0.06 mm. The simulations were carried out on the supposition that the acoustic adjustment layers 5a to 5c were made of a material with the same acoustic impedance as the acoustic lens 4.

In the acoustic lens 6 used in the simulations of FIG. 5(a), the first acoustic lens portion 6a has a first curvature of 16.36 mm and the second acoustic lens portion 6b has a second curvature of 8.4 mm. The acoustic lens 4 used in the simulations of FIG. 5(b) has a curvature of 16.36 mm.

Figure 5:
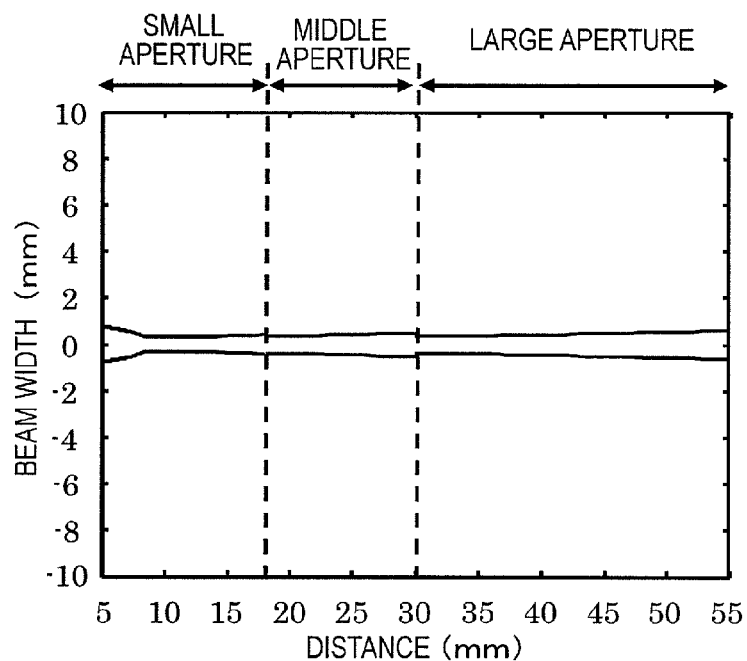
FIGS. 5(a) and 5(b) show the results of simulations on the beams transmitted by sound probes according to the first and second embodiments.
Figure 5:
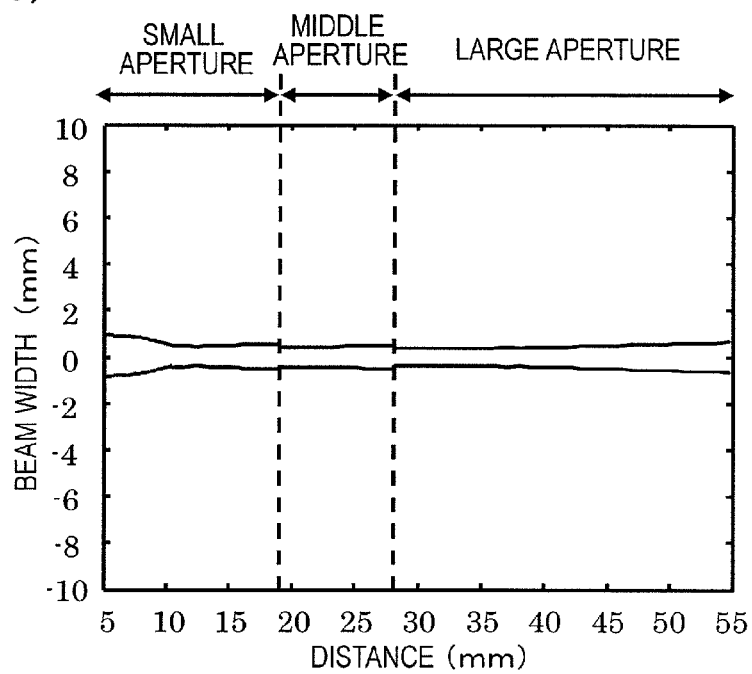

As in the first embodiment described above, the results of the simulations shown in FIGS. 5(a) and 5(b) were obtained in the following manner. Specifically, a position with the highest ultrasonic wave intensity at a certain depth level (i.e., at a certain position in the Z-axis direction) was supposed to be the origin (0 dB) and a position (or distance (mm)) with an ultrasonic wave intensity corresponding to −3 dB with respect to the origin was plotted in the x-axis direction at that position in the Z-axis direction. By setting these positions at an arbitrary depth level, a beam profile in the depth direction was obtained. That is why in FIG. 5, the abscissa indicates the distance (mm) as measured from the sound probe 1 in the depth direction in which ultrasonic waves are transmitted and the ordinate indicates the width (mm) of a beam at which an intensity of −3 dB can be obtained with respect to the center of the beam.

Also, the results of the simulations shown in FIGS. 5(a) and 5(b) were obtained by getting data about depth levels of 5 to 55 mm in the respective cases of small, middle and large apertures, extracting data about ranges where the transmitted beams with the small, middle and large apertures were sufficiently converged, and synthesizing those data together.

As can be seen from the results of simulations shown in FIGS. 5(a) and 5(b), according to this embodiment, the beam width can be further narrowed in the range where the small aperture is used, specifically, in the range from a relatively shallow level (of around 7 mm) to a depth level of around 27 mm.

Figure 6:
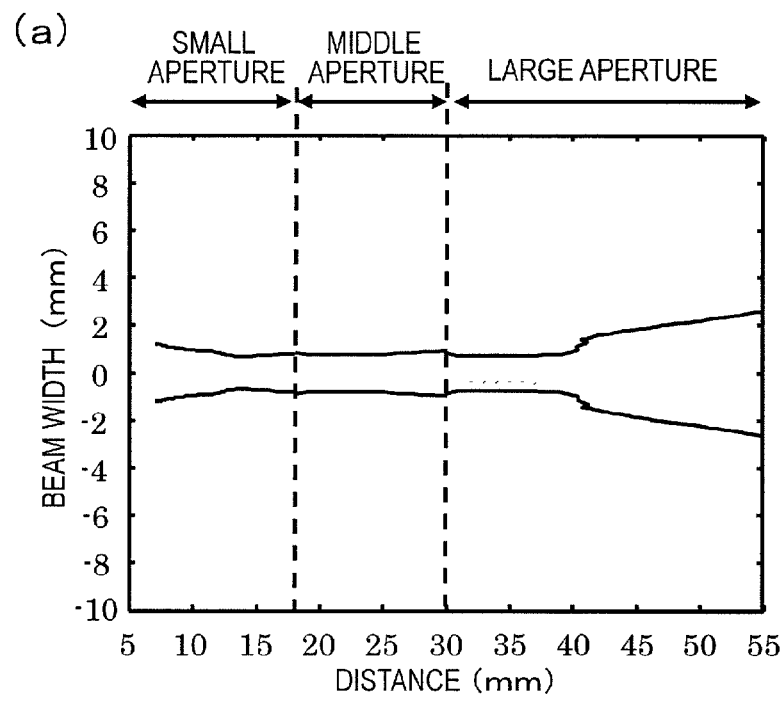
FIGS. 6(a) and 6(b) show the results of simulations on the beams transmitted by other sound probes according to the first and second embodiments.
Figure 6:
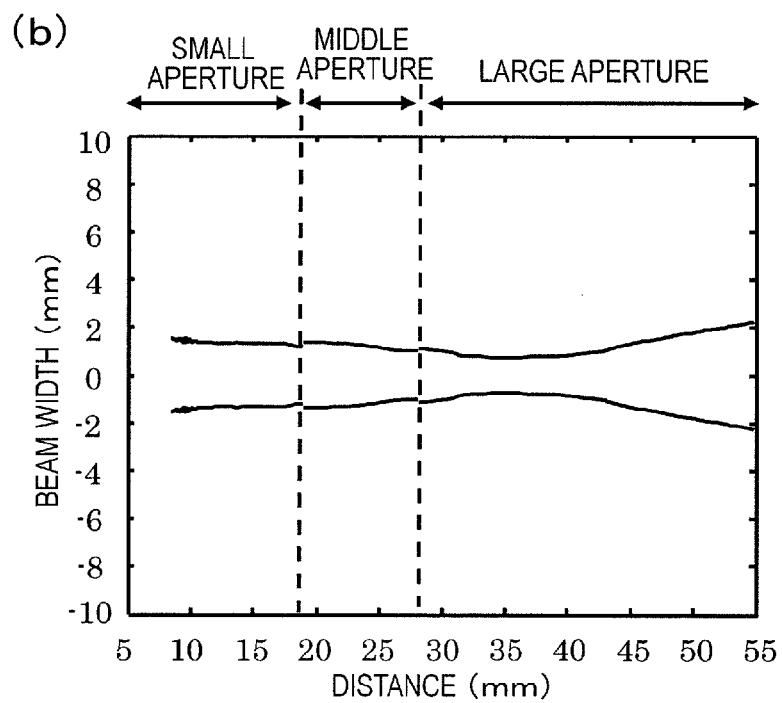

To analyze the effects of this embodiment more minutely, a distance (mm) with an ultrasonic wave intensity corresponding to −12 dB with respect to the center of the beam (0 dB) was plotted. The results are shown in FIGS. 6(a) and 6(b). Specifically, FIG. 6(a) shows the results of simulations on the beam shape obtained in the x-axis direction by the sound probe 1 of this embodiment. On the other hand, FIG. 6(b) shows the results of simulations on the beam shape obtained in the x-axis direction by the sound probe 1 of the first embodiment.

As can be seen from the results of simulations shown in FIGS. 6(a) and 6(b), the beam can be converged sufficiently according to this embodiment at depth levels of around 7 mm to around 30 nm. At levels deeper than 40 mm, the transmitted beam of this embodiment becomes a little wider than that of the first embodiment. Considering that the transmission frequency is approximately 9 MHz, however, at such a depth, the image quality would deteriorate more significantly due to a frequency dependent attenuation rather than due to the influence of such widening of the transmitted beam.

As can be seen, the sound probe of this embodiment uses not only the acoustic adjustment layers 5a to 5c but also the acoustic lens 6 comprised of the first acoustic lens portion 6a of which the surface shape has a first curvature and the second acoustic lens portion 6b which has a second surface shape to cope with a smaller aperture. As a result, the shape of the transmitted beam at a relatively shallow level can be improved with the beam width at a relatively deep level kept narrow. Consequently, an ultrasonic image of better image quality can be obtained.

Figure 7:
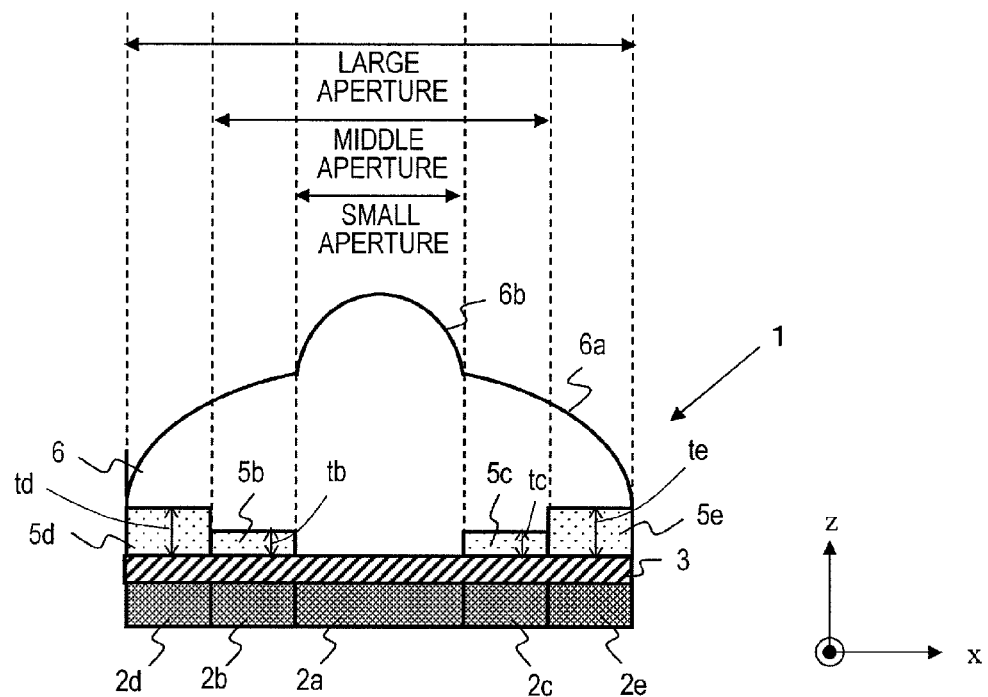
FIG. 7 is a cross-sectional view illustrating another example of the second embodiment.

As shown in FIG. 7, the acoustic adjustment layer may also be made of a material with a lower sound velocity than the acoustic lens 4, and the acoustic adjustment layers 5 $d$ and 5 $e$ associated with the transducer elements 2 $d$ and 2 $e$ located at the end portions in the x-axis direction may be thicker than the acoustic adjustment layers 5 $b$ and 5 $c$ associated with the transducer elements 2 $b$ and 2 $c$ located at the center portion in the x-axis direction.

In this embodiment, the acoustic lens 6 has a configuration in which the second acoustic lens portion 6$b$ which faces the transducer element 2$a$ and which has a surface shape with the second curvature is arranged on the first acoustic lens portion 6$a$ having a surface shape with the first curvature. However, the beam shape can be further improved by adopting a configuration in which acoustic lens portions with mutually different curvatures are provided for respective aperture widths.

Figure 8:
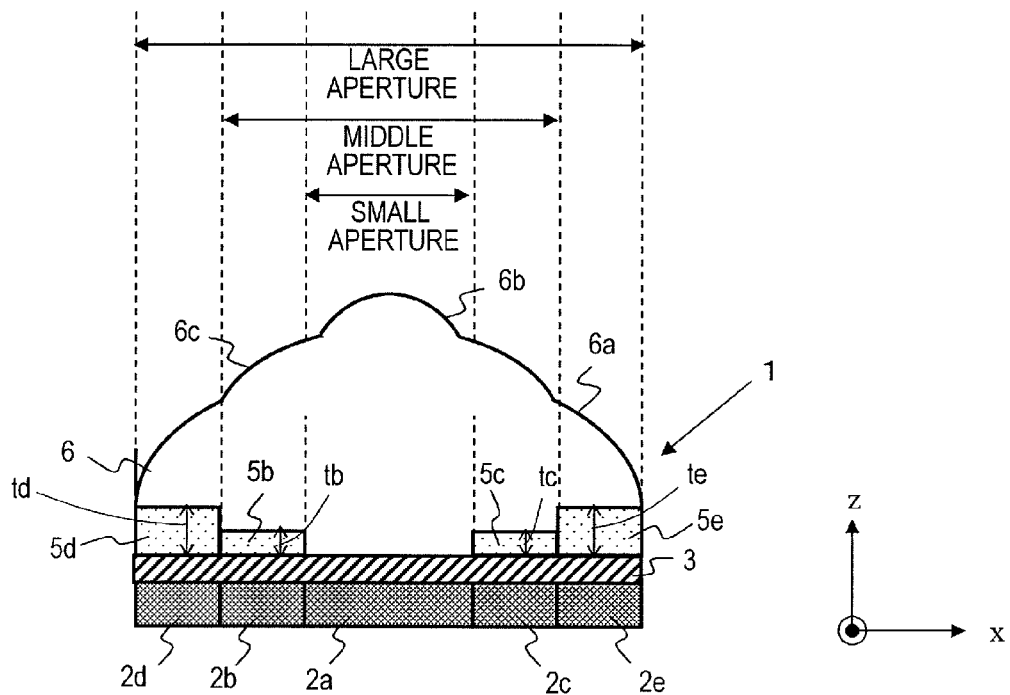
FIG. 8 is a cross-sectional view illustrating still another example of the second embodiment.

Specifically, as shown in FIG. 8, the acoustic lens 6 may include first, second and third acoustic lens portions 6$a$, 6$b$ and 6$c$. The first acoustic lens portion 6$a$ faces the transducer elements 2$a$ to 2$e$ and has a surface shape with a first curvature. The third acoustic lens portion 6$c$ faces the transducer elements 2$a$ to 2$c$ and is arranged on the first acoustic lens portion 6$a$. The surface of the third acoustic lens portion 6$c$ has a third curvature. The second acoustic lens portion 6$b$ faces the transducer element 2$a$ and is arranged on the third acoustic lens portion 6$c$. The surface of the second acoustic lens portion 6$b$ has a second curvature. The second curvature is larger than the third curvature, and the third curvature is larger than the first curvature.

According to the first and second embodiments described above, a plurality of acoustic adjustment layers are arranged between transducer elements and an acoustic lens, and have their thicknesses varied, thereby reducing the difference in the amount of time it takes for ultrasonic waves transmitted from the respective transducer elements to get converged by the acoustic lens and reach a certain depth level in the subject and shaping the transmitted beam into a narrower one. That is to say, the first and second embodiments described above are partly characterized in that the amount of time it takes for the ultrasonic waves transmitted from the respective transducer elements to reach a certain depth level is controlled using acoustic adjustment layers made of a material with a different sound velocity from the material of the acoustic lens. That is why the ultrasonic wave arrival time could be controlled by any other structure instead of using such varied thicknesses of the acoustic adjustment layers.

For example, the amount of time it takes for those ultrasonic waves to reach a certain depth level may also be controlled by making those acoustic adjustment layers that the ultrasonic waves transmitted from the transducer elements enter of materials with multiple different sonic velocities. That is to say, the amount of time it takes for those ultrasonic waves to reach a certain depth level can be controlled by changing the material and/or thickness of the acoustic adjustment layers. Thus, the arrival time may be controlled with the material and thickness of the acoustic adjustment layers changed in combination.

If the acoustic adjustment layers are made of multiple materials with higher sonic velocities than the acoustic lens, then the materials of the acoustic adjustment layers may be determined so that the closer to the center in the x-axis direction the transducer element associated with an acoustic adjustment layer is (i.e., the closer to the center in the x-axis direction the acoustic adjustment layer to propagate the ultrasonic wave transmitted from the transducer element is), the higher the sound velocity of the material of that acoustic adjustment layer is. Then, those ultrasonic waves transmitted simultaneously from the respective transducer elements can reach a certain depth level at as close to the same time as possible.

On the other hand, if the propagating mediums are made of multiple materials with lower sonic velocities than the acoustic lens, then the materials of the acoustic adjustment layers may be determined so that the closer to the center in the x-axis direction the transducer element associated with an acoustic adjustment layer is (i.e., the closer to the center in the x-axis direction the acoustic adjustment layer to propagate the ultrasonic wave transmitted from the transducer element is), the lower the sound velocity of the material of that acoustic adjustment layer is. Then, those ultrasonic waves transmitted simultaneously from the respective transducer elements can reach a certain depth level at as close to the same time as possible.

In that case, the acoustic impedances of those materials of the acoustic adjustment layers and the material of the acoustic lens are suitably either equal or close to each other.

The sound velocity of the material of each acoustic adjustment layer may be adjusted by changing the amount of a filler such as zinc oxide to be added to silicone rubber as described above.

Embodiment 3

In the first and second embodiments described above, by providing acoustic adjustment layers between transducer elements and an acoustic lens, the phase of ultrasonic waves transmitted from the respective transducer elements (i.e., the amount of time it takes for those ultrasonic waves to reach a certain depth level) is controlled, and the transmitted beam is shaped into a narrower one.

In this embodiment, transducer elements, each having a surface which is depressed with respect to the outside and transmitting an ultrasonic wave from that concave surface, are used, and the arrival times of pulses of those ultrasonic waves generated from the inner and outer transducer elements or their phase is controlled so that the ultrasonic waves transmitted simultaneously from those transducer elements can reach a certain depth level at as close to the same time as possible.

Figure 9:
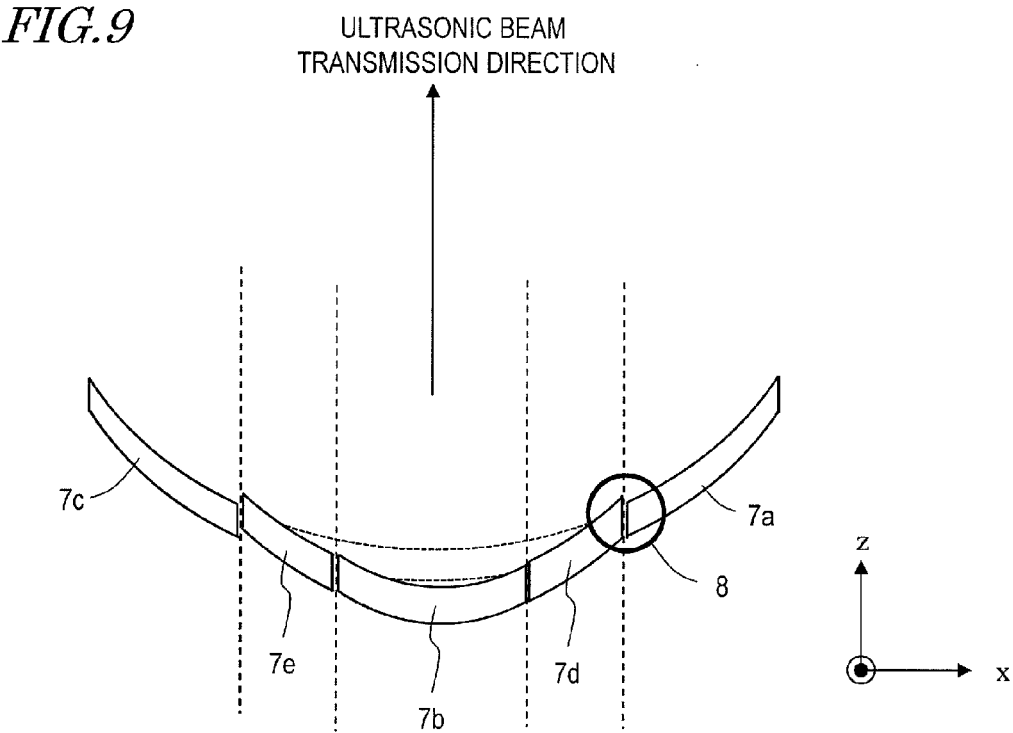
FIG. 9 is a cross-sectional view illustrating a portion of an sound probe as a third embodiment of the present invention.

As shown in FIG. 9, the sound probe of this embodiment includes transducer elements 7$a$ to 7$e$, which have been divided into five and arranged in the x-axis direction. Each of these transducer elements 7$a$ to 7$c$ has a surface which is depressed in the z-axis direction with respect to the outside (i.e., with respect to the subject). Specifically, these transducer elements 7$a$ to 7$e$ are arranged as follows. The transducer element 7$b$ is arranged at the center in the x-axis direction. The transducer elements 7$d$ and 7$e$ are arranged so as to interpose the transducer element 7$b$ between them. And the transducer elements 7$a$ and 7$c$ are arranged so as to interpose the transducer elements 7$b$, 7$d$ and 7$e$ between them. Also, these transducer elements 7$a$ to 7$e$ are arranged so that the farther away from the transducer element 7$b$ at the center a transducer element is, the closer to the subject (closer to the outside) that transducer element is located in the z-axis direction. Thus, these transducer elements 7$a$ to 7$e$ are arranged so that their ultrasonic wave emission surface forms a depressed portion overall.

Furthermore, the outer transducer elements have an ultrasonic wave transmission face with a smaller curvature than the transducer element located at the center in the x-axis direction. Specifically, the curvature of the transducer element 7$b$ is larger than that of the transducer elements 7$d$ and 7e, and the curvature of the transducer elements 7d and 7e is larger than that of the transducer elements 7a and 7c.

Figure 10:
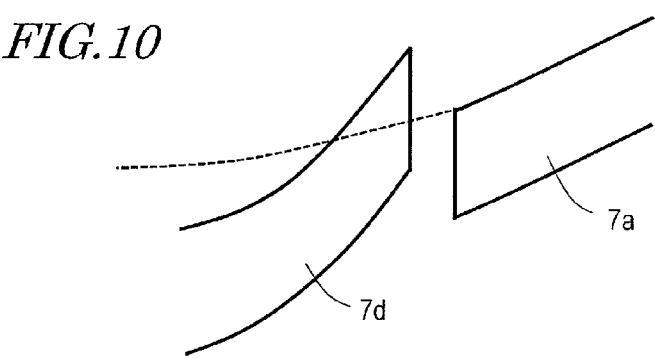
FIG. 10 is a partially enlarged view of FIG. 9.
Figure 11:
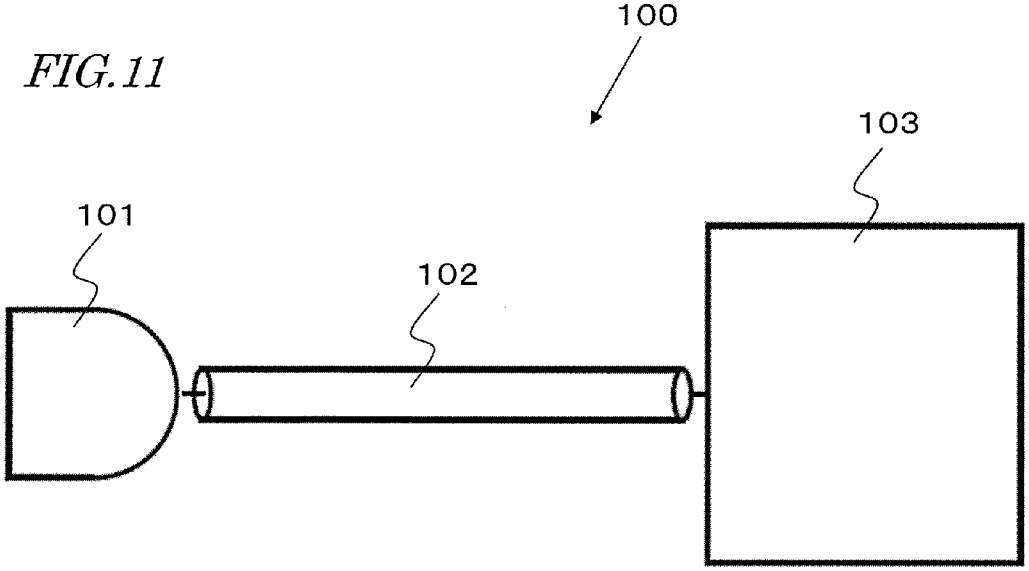
FIG. 11 is a view generally illustrating a configuration for a conventional ultrasonic diagnostic apparatus.
Figure 12:
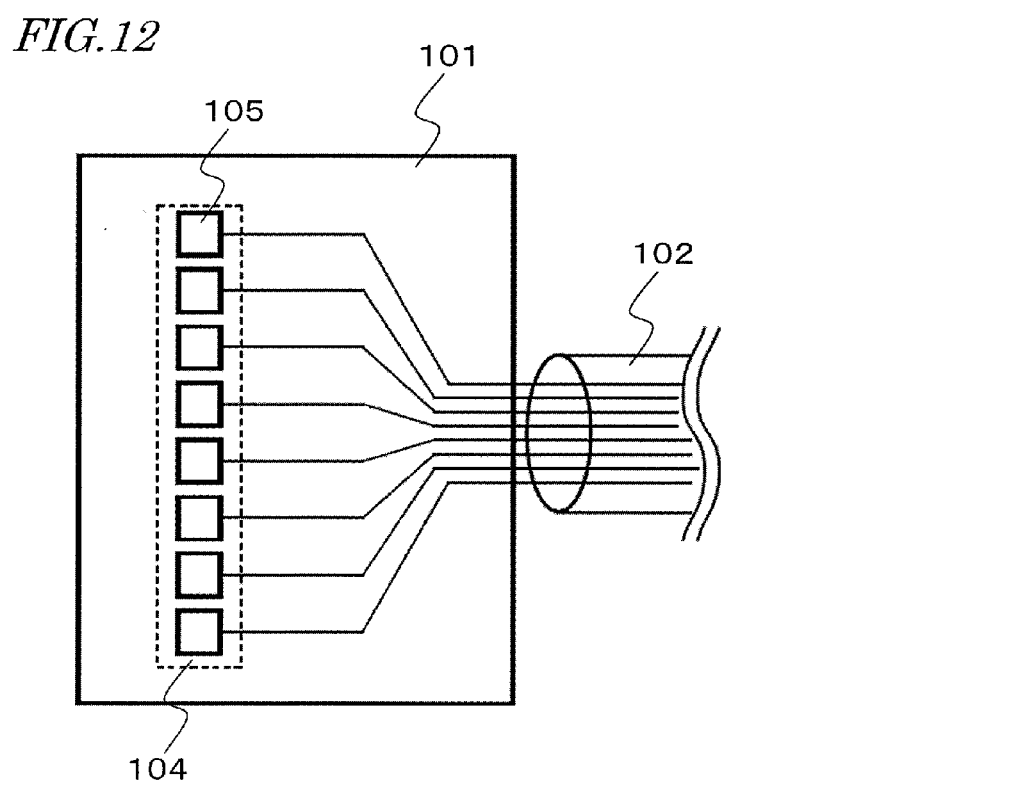
FIG. 12 is a schematic representation illustrating a configuration for a conventional ultrasonic sound probe.
Figure 13:
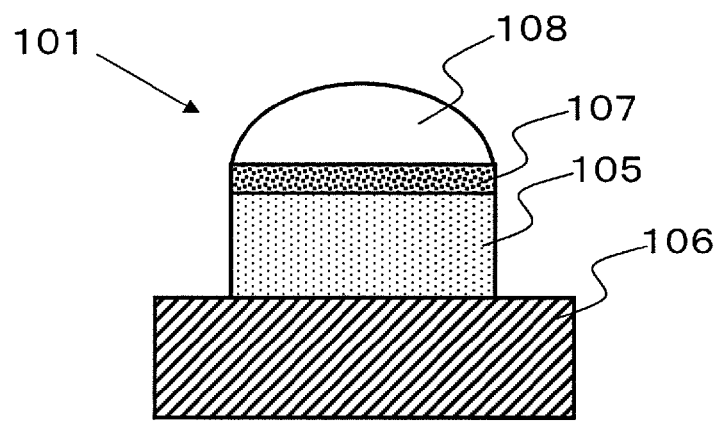
FIG. 13 is a cross-sectional view illustrating another conventional sound probe.

FIG. 10 illustrates a transducer element boundary 8 between the transducer elements 7a and 7d. In the transducer elements on the whole, the outer transducer element 7a is located more distant from the subject than the inner transducer element 7d is. Meanwhile, at the transducer element boundary 8 where the transducer elements 7a and 7d are located close to each other, a part of the transducer element 7d is arranged closer to the subject than the transducer element 7a is. As a result, the ultrasonic pulse radiated from the transducer element 7d that is closer to the center can be synchronized with other pulses, and therefore, the beam shape obtained can be as good as that of the first embodiment. In addition, the acoustic lens as described for the first to third embodiments is no longer needed and a narrow transmitted beam can be generated using a simple configuration.

INDUSTRIAL APPLICABILITY

The sound probe according to the present disclosure can minimize deformation in beam shape at a deep level even if the aperture is widened in the elevation direction, and therefore, can generate a beam with excellent azimuthal resolution. As a result, a good signal can be provided for the body of an ultrasonic diagnostic apparatus, and the image quality of the resultant ultrasonic image can be improved.

Consequently, the present disclosure can be used effectively as an sound probe that can obtain an ultrasonic image of high image quality in making a medical diagnosis, in particular.

REFERENCE SIGNS LIST 1 sound probe
2a, 2b, 2c, 2d, 2e transducer element
3 acoustic matching layer
4, 6 acoustic lens
5a, 5b, 5c acoustic adjustment layer
6a first acoustic lens portion
6b second acoustic lens portion
7a, 7b, 7c, 7d, 7e transducer elements
8 transducer element boundary
100 ultrasonic diagnostic apparatus
101 sound probe
102 cable
103 apparatus body
104 array of transducer elements
105, 105a, 105b, 105c transducer elements
107 acoustic matching layer
108 acoustic lens

The invention claimed is:

1. An ultrasound probe comprising:
an array of transducer elements in which a plurality of transducer elements are arranged two-dimensionally in a first direction corresponding to an elevation direction and in a second direction corresponding to an azimuth direction that is different from the first direction, wherein the array of transducer elements makes an interconversion between an electric pulse and an ultrasonic wave;
an acoustic lens which has a convex surface in a transmission direction of the ultrasonic wave on a cross section that is parallel to the first direction and the transmission direction and which converges ultrasonic waves transmitted from the plurality of transducer elements;
at least two acoustic adjustment layers which are made of a material that has a different sound velocity from the acoustic lens, which are respectively arranged between at least two of the transducer elements of a row of the transducer elements that are arranged in the first direction and the acoustic lens, and of which at least one of the material and a thickness of each of the at least two acoustic adjustment layers in the transmission direction are different from each other, wherein both end surfaces in the first direction of each of the acoustic adjustment layers are arranged so as to substantially coincide with both end surfaces in the first direction of respective transducer elements, and no acoustic adjustment layer is arranged between at least one of the transducer elements of the row of transducer elements and the acoustic lens; and
an acoustic matching layer through which the ultrasonic waves transmitted from the plurality of transducer elements pass.

2. The ultrasound probe of claim 1, wherein the acoustic adjustment layers are made of a material which has a higher sound velocity than the acoustic lens, and
the closer to the center of the array of transducer elements in the first direction the transducer element associated with an acoustic adjustment layer is, the greater the thickness is.

3. The ultrasound probe of claim 2, wherein the at least two acoustic adjustment layers include:
a first acoustic adjustment layer which is associated with the transducer element that is located at the center of the array of transducer elements in the first direction; and
a second acoustic adjustment layer which is adjacent to the first acoustic adjustment layer in the first direction, and the first acoustic adjustment layer is thicker than the second acoustic adjustment layer.

4. The ultrasound probe of claim 1, wherein the acoustic adjustment layers are made of a material which has a lower sound velocity than the acoustic lens, and
the closer to the center of the array of transducer elements in the first direction the transducer element associated with an acoustic adjustment layer is, the smaller the thickness is.

5. The ultrasound probe of claim 4, wherein the at least two acoustic adjustment layers include:
a first acoustic adjustment layer which is associated with the transducer element that is located at the center of the array of transducer elements in the first direction; and
a second acoustic adjustment layer which is adjacent to the first acoustic adjustment layer in the first direction, and the first acoustic adjustment layer is less thick than the second acoustic adjustment layer.

6. The ultrasound probe of claim 1, wherein the acoustic adjustment layers are made of a material which has a higher sound velocity than the acoustic lens, and
the closer to the center of the array of transducer elements in the first direction the transducer element associated with an acoustic adjustment layer is, the higher the sound velocity of the material of that acoustic adjustment layer is.

7. The ultrasound probe of claim 1, wherein the acoustic adjustment layers are made of a material which has a lower sound velocity than the acoustic lens, and
the farther away from the center of the array of transducer elements in the first direction the transducer element associated with an acoustic adjustment layer is, the lower the sound velocity of the material of that acoustic adjustment layer is.

8. The ultrasound probe of claim 1, wherein the acoustic adjustment layers are made of a material having an acoustic impedance which is either the same as, or close to, the acoustic impedance value of the acoustic lens.

9. The ultrasound probe of claim 1, wherein the acoustic lens includes:
- a first acoustic lens portion, of which the surface shape has a first curvature on a cross section which is parallel to the first direction and the transmission direction; and
- a second acoustic lens portion which is arranged on the first acoustic lens portion in the transmission direction and of which the surface shape has a second curvature.

10. The ultrasound probe of claim 9, wherein the second curvature is larger than the first curvature.

11. The ultrasound probe of claim 9, wherein the first and second acoustic lens portions are made of the same material.

12. An ultrasound probe comprising:
- an array of transducer elements in which a plurality of transducer elements are arranged two-dimensionally in a first direction corresponding to an elevation direction and in a second direction corresponding to the azimuth direction that is different from the first direction, wherein the array of transducer elements makes an inter-conversion between an electric pulse and an ultrasonic wave;
- an acoustic lens which has a convex surface in a transmission direction of the ultrasonic wave on a cross section that is parallel to the first direction and the transmission direction and which converges ultrasonic waves transmitted from the plurality of transducer elements;
- an acoustic adjustment layer which is made of a material that has a different sound velocity from the acoustic lens and which is arranged between one of the transducer elements of a row of the transducer elements arranged in the first direction and the acoustic lens, wherein both end surfaces in the first direction of the acoustic adjustment layer are arranged so as to substantially coincide with both end surfaces in the first direction of the one of the transducer elements, and no acoustic adjustment layer is arranged between at least some of the transducer elements of the row of transducer elements and the acoustic lens; and
- an acoustic matching layer through which the ultrasonic waves transmitted from the plurality of transducer elements pass.

* * * * *